United States Patent [19]

Patel

[11] Patent Number: 4,577,621

[45] Date of Patent: Mar. 25, 1986

[54] ENDOSCOPE HAVING NOVEL PROXIMATE AND DISTAL PORTIONS

[76] Inventor: Jayendrakumar I. Patel, 502 Rector St., Valdese, N.C. 28690

[21] Appl. No.: 677,558

[22] Filed: Dec. 3, 1984

[51] Int. Cl.$^4$ .............................................. A61B 1/06
[52] U.S. Cl. .......................................................... 128/4
[58] Field of Search .................................... 128/4, 6, 7

[56] References Cited

U.S. PATENT DOCUMENTS

| | | | |
|---|---|---|---|
| 3,610,231 | 10/1971 | Takahashi et al. | 128/6 |
| 3,788,304 | 1/1974 | Takahashi | 128/6 |
| 3,866,601 | 2/1975 | Russell | 128/4 |
| 4,141,364 | 2/1979 | Schultze | 128/4 X |
| 4,148,307 | 4/1979 | Utsugi | 128/4 |
| 4,176,662 | 12/1979 | Fraser | 128/6 |
| 4,207,872 | 6/1980 | Meiri et al. | 128/4 |
| 4,273,111 | 6/1981 | Tsukaya | 128/6 |
| 4,292,961 | 10/1981 | Kawashima | 128/6 |
| 4,329,995 | 5/1982 | Anthracite | 128/4 X |
| 4,366,810 | 1/1983 | Slanetz, Jr. | 128/6 |

*Primary Examiner*—William H. Grieb
*Attorney, Agent, or Firm*—Roy B. Moffitt

[57] ABSTRACT

Three embodiments of an improved endoscope: The first embodiment is composed of a flexible tube member, the proximate end portion of which is attached to and in optical communication with a control unit; and, a second flexible tube member partially circumscribing the first tube member, one terminal end portion of which is (i) affixed to the outer surface of the first flexible tube at a point other than the distal portion and (ii) adapted to expand and contract along its own and the longitudinal axis of the first flexible tube member. The second embodiment contains a control unit, first, second and flexible tube members and in addition a third tube member. The third tube member has (i) a terminal portion affixed to the first tube member at a point other than at a distal portion and (ii) the balance thereof spaced apart from and circumscribes a part of the first and a portion of the second flexible tube member. One terminal free end of the second flexible tube is slideably received within the third tube member. The third embodiment contains a control unit, first and second flexible tube members; the second flexible tube member is not attached to the first flexible tube and has a terminal end portion composed of an outward flaring sidewall forming an angle with the longitudinal axis of the balance of the second flexible tube.

13 Claims, 22 Drawing Figures

PRIOR ART

PRIOR ART

ENDOSCOPE HAVING NOVEL PROXIMATE AND DISTAL PORTIONS

BACKGROUND OF THE INVENTION

The invention relates to a medical examining instrument (an endoscope) used to view the internal sidewalls of the organs of a human or animal body from a point outside of such body. More particularly, the invention is an endoscope that has an elongated tube member used to be inserted through linear, nonlinear, curved and/or looped passages within a human and or animal body so that the sidewalls of such body can be visually observed through a viewing apparatus located outside of the body. One of the drawbacks encountered in the use of prior art endoscopes, especially in humans, is the pain and discomfort experienced by the patient. This, coupled with the high degree of skill a medical practitioner must have in order to insert and manipulate prior art endoscopes into a human cavity, limits their widespread use. This is unfortunate because deep penetration into a human organ is possible with an endoscope and more often than not the medical practitioner desires (for professional and ethical reasons) to make an examination of the deepest regions of the organ in question by advancing the endoscope to its physical limits.

In many cases, it is not only desirable but professionally required that a medical practitioner visually examine the internal organs or passages of a human and/or animal body for diagnosis, biopsy, or for removal of obstructions, foreign bodies or stones without cutting open the patient and the organ to be examined. One method of visually examining the internal organs of a patient without surgery is to insert the flexible fiber optic portion of an endoscope into the body through a natural or a surgically prepared opening. The distal (inspection) portion of the instrument (in optical communication with a control unit) illuminates the area and also permits inspection through a viewing device from outside of the body under examination. Endoscopes are well known in the prior art and details of the construction of a flexible fiber optic endoscope are set forth in U.S. Pat. Nos. 3,610,231; 3,788,304; 4,273,111 and 4,292,961, the disclosures of which are herein set forth as if faithfully reproduced.

Notwithstanding the fact that endoscopes are well known to the medical profession, experienced operators often experience problems in properly placing the distal end of the instrument in the deep areas of a human or animal body. Body passages, often nonlinear, are made of soft, stretchable, flexible, foldable, pressure and pain sensitive tissue. Invariably they have bends or loops which are difficult to negotiate without causing pain to the patient. U.S. Pat. Nos. 4,292,961 and 4,366,810 both recognize these difficulties and disclose complex apparatus and methods in an attempt to solve these problems. They are complex, expensive, difficult to manipulate and require a high degree of skill to use. It is towards the solution of the above stated problems that the instant invention is directed.

SUMMARY OF THE INVENTION

The invention has three embodiments. The first embodiment is composed of a prior art endoscope control unit and first and second flexible tube members both having a body portion and proximate and distal end portions. The proximate end portion of the first flexible tube member is attached to and in optical communication with the control unit and the body portion, which is in optical communication with the distal portion. The distal end portion is movable and has a free end. The second flexible tube member partially circumscribes the first tube member, is composed of a proximate end portion connected by a body portion to a distal end portion. Its distal end portion is affixed to the outer surface of the first flexible tube at a point other than the distal portion of the first flexible tube member by a means adapted to expand and contract along its own and longitudinal axis of the first flexible tube member.

It is inherent with most organs into which the flexible tube member of an endoscope is inserted to "clamp down" on the tube, once the insertion begins. This "clamping" works to the benefit of the operator of the embodiment of the present invention, which is basically a prior art endoscope with two flexible tubes, one nested coaxially inside of the other. The innermost tube (the one containing the optical means) allows the operator to see the sidewalls of the organ being examined. The outermost tube is connected to the innermost tube by an accordion type flexible member, which allows the outermost flexible tube member to be reciprocated back and forth by compressing and expanding the accordion type distal portion of the second flexible tube member. When this accordion distal portion is compressed, the operator then pushes on the innermost tube, i.e., first flexible tube member nested inside of the second flexible tube, and thus stretches out the compressed accordion type distal portion. This action advances the distal end portion of the first flexible tube the length the accordion type member had previously been compressed. By successive contractions and expansions, an "inchworm" type advance of the distal portion of the first flexible tube can be made through the organ cavity in measured increments. Such progress uses the clamping propensity of the organ on the second flexible tube to aid and assit the advancement of the distal portion of the innermost (first) flexible tube member, i.e., the "business end" of the endoscope with its viewing means. Complementary to the "clamping" action the operator holds stationary the second tube while advancing the first and holds stationary the first tube while advancing the second, all from a point outside of the body cavity.

The second embodiment of the invention takes advantage of the same principle (the organ clamping propensity) as does the first embodiment but is non-collapsible in nature compared to the previously described embodiment. It also has a control unit and first and second flexible tube members essentially the same as that first embodiment. Furthermore, the second flexible tube member partially circumscribes the first tube member, the first tube member being nested inside of the second flexible tube member. In addition, however, this second embodiment contains a third tube member, one terminal portion of which is affixed to the first tube member at a point other than the distal portion. The balance of the sidewall of the third tube member is spaced apart from and circumscribes the first and the distal portion of the second flexible tube member. The terminal free end of the distal end portion of the second flexible tube is slideably received within the third tube member and it can be reciprocated between that point of where the third tube member is affixed to the first tube member and the terminal free edge of the opposite end of the third tube member itself. Because of this reciprocation feature, the first flexible tube member (along with the third tube member) is advanced while holding stationary (outside of the body) the second flexible tube member and then the second tube member can be advanced while holding stationary (outside of the body) the first tube member to the extent that its distal free end is spaced apart from a point where the third tube member is attached to the second tube member. This process is repeated over and over again in measured increments, as was the case in the previously described embodiment, thereby advancing the business (distal) end of the first tube member to the desired location.

The third embodiment (hereinafter referred to as the "dog bone" embodiment) comprises a control unit, a first and a second flexible tube members, both of which are composed of proximate, body and distal portions. The distal portion of the first flexible tube member is in optical communication, via its body and proximate portions, with the control unit. As with the other embodiments, the first tube member is coaxially nested inside of the second tube member. The distal end portion of the second flexible tube member is comprised of an outward flaring sidewall forming an angle with the longitudinal axis of the balance of the second flexible tube. Such outward flaring sidewall has a thickness greater than the thickness of the balance of the second flexible tube member and thus gives an overall configuration a "dog bone" look. Here again, the second flexible tube member (with the first flexible tube member nested therein) is inserted into the organ. As the second flexible tube member is held stationary by the operator outside of the body, the first flexible tube member is advanced a short distance and then rested. Then the second flexible tube member is further inserted into the organ as far as the terminal free edge of the distal end of the first flexible tube member while the first tube member is held stationary outside of the body. This process is repeated until the distal end of the first flexible tube member (the viewing portion of the endoscope) has reached the desired deep portion of the cavity sought to be examined.

Either one of the three embodiments overcomes the problem inherent in prior art endoscopes, i.e., even though the distal end of a prior art endoscope can be pushed towards the desired direction the force or push applied to advance the endoscope is not necessarily transmitted to the distal end when the distal end has gone beyond a loop or a curved passageway. For example, but not by way of limitation, insertion of a prior art colonscope (a variety of endoscope) into the deeper areas of the human colon poses many difficulties due to the anatomy of the colon. The human colon has curves or bends (known as loops) and is made up of soft, stretchable, foldable, very pain sensitive tissues. In addition, it is affixed to the abdomen in some places and free in others. After the distal end of the colonscope passes through the initial curve, which is rather close to the rectum, further pushing of the scope results in enlargement of the curve rather than the desirable advancement of the distal portion. This results in the stretching of the colon and is very painful to the patient. One method, known to the prior art, of facilitating the further advancement of a colonscope of such a situation is to forcefully straighten out the colon by a skillful manipulation of the instrument. This procedure is very painful for the patient and medical professionals must receive highly specialized training to learn such manuevers. Consequently, such endoscopy is rather expensive and limited in use. To the contrary, the three disclosed embodiments of this invention make it unnecessary to straighten out a colon or other curved or looped passages of a body cavity to advance an endoscope to its desired depth, thus solving one of the inherent problems of prior art endoscopes. In addition they avoid entrapment of organ tissue matter between the two tube members.

DETAILED DESCRIPTION OF THE INVENTION

Figure 1A:
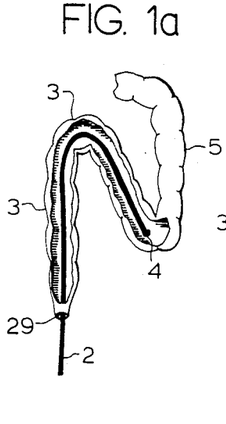
FIGS. 1(a), 1(b), 1(c), 1(d) and 1(e) are graphic representations of a step by step procedure employing a prior art endoscope to straighten out the first encountered loop in a human colon in preparation of advancing same to the deeper regions of the organ.
Figure 1B:
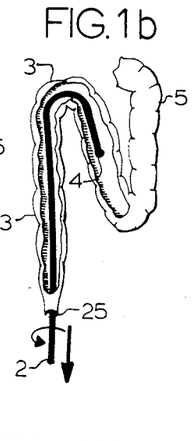
Figure 1C:
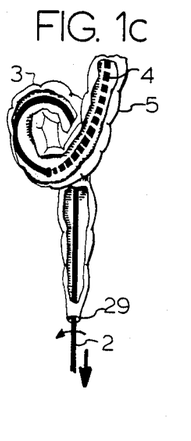
Figure 1D:
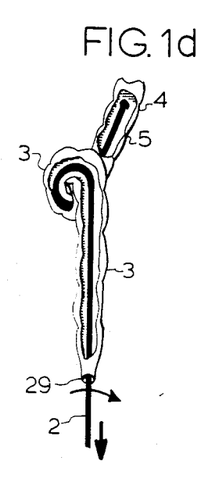
Figure 1E:
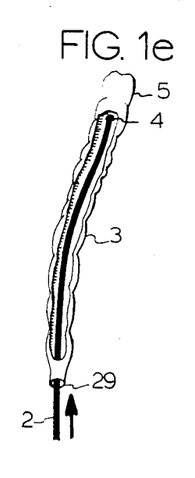

The use of prior art endoscopes (particularly colonscopes) and the problems encountered when in use are best illustrated by reference to FIGS. 1(a), 1(b), 1(c), 1(d) and 1(e), where a technique (not necessarily the only technique) for straightening out a colon loop is shown. As mentioned earlier, an attempt to advance an endoscope through this first loop only results in its enlargement; therefore, it must be first straightened out. While there are various techniques to "straighten out a colon loop", one that is shown in the previously referenced figure numerals is illustrative. Distal tube portion 4 of the endoscope is inserted through anus 29 into the sigmoid portion 3 of the colon and forms a long loop with an acute angle at the junction of the sigmoid 3 and descending colon 5. The next step is to withdraw the instrument to the mid-sigmoid colon position as shown in FIG. 1(b), leaving a free segment of the sigmoid portion of the colon 3 for subsequent rotation. Subsequently the operator rotates counter clockwise the sigmoid loop producing an alfa loop pattern as shown in FIG. 1(c) and then removes the alfa loop by rotating the endoscope tube portion clockwise and simultaneously withdrawing the instrument [FIG. 1(d)], thereby producing a straightened sigmoid colon as shown in FIG. 1(e). The ability to successfully perform such endoscopy procedures with expertise and minimal patient discomfort depends largely upon the degree of technical skill and experience of the operator. In order to attain these skills, there is, of course, no substitute for actual "hands on" patient experience. The finesse required to perform these manuevers can only be achieved by repetitive training and unfortunately with a great deal of discomfort and pain to the patient.

Figures 2, 3:
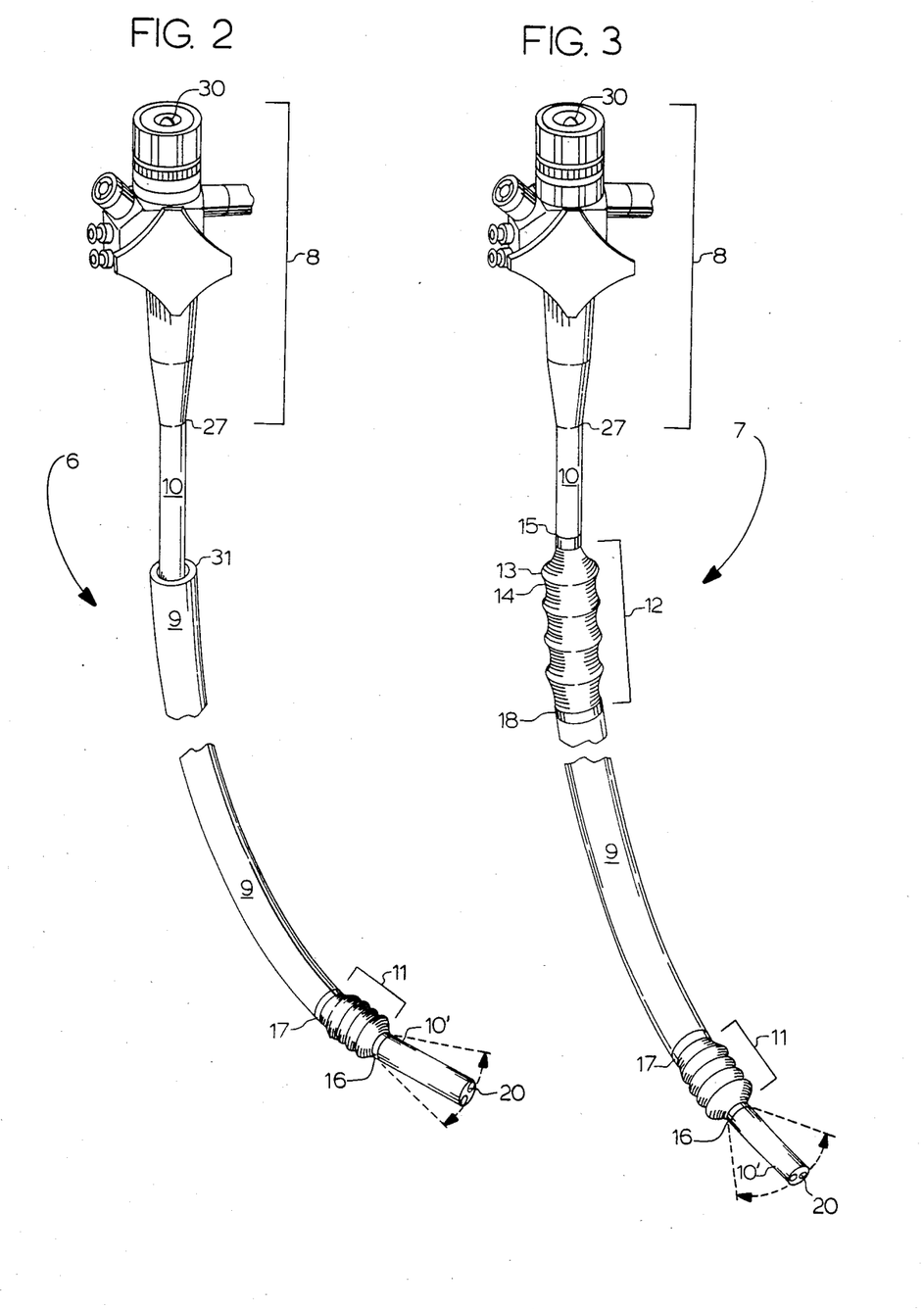
FIG. 2 is an oblique external view of the first embodiment of the invention.
FIG. 3 is an oblique external view of the second embodiment of the invention.
Figure 4A:
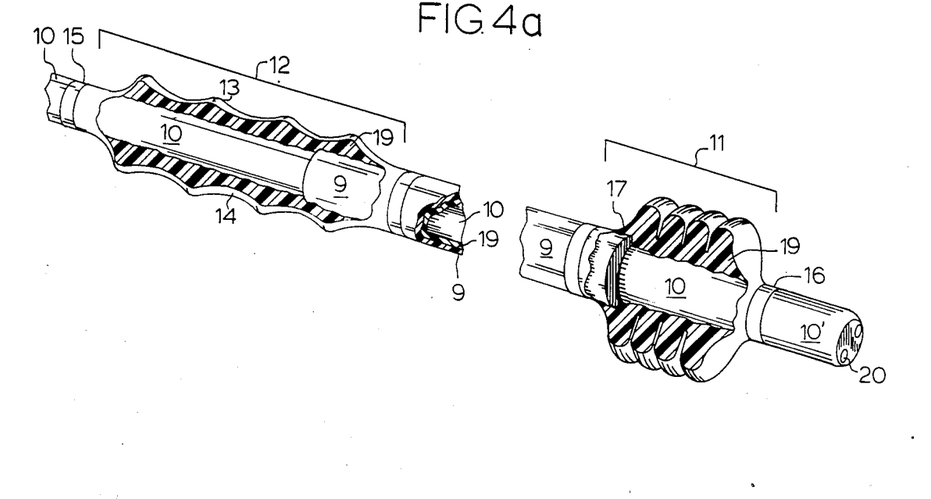
FIGS. 4(a) and 4(b) are oblique partial cutaway views of the distal and proximate end portions of the embodiment shown in FIG. 3, it being understood that the distal end portion of the embodiment shown in FIG. 2 operates in the same manner as element 11 of FIGS. 4(a) and (b).
Figure 4B:
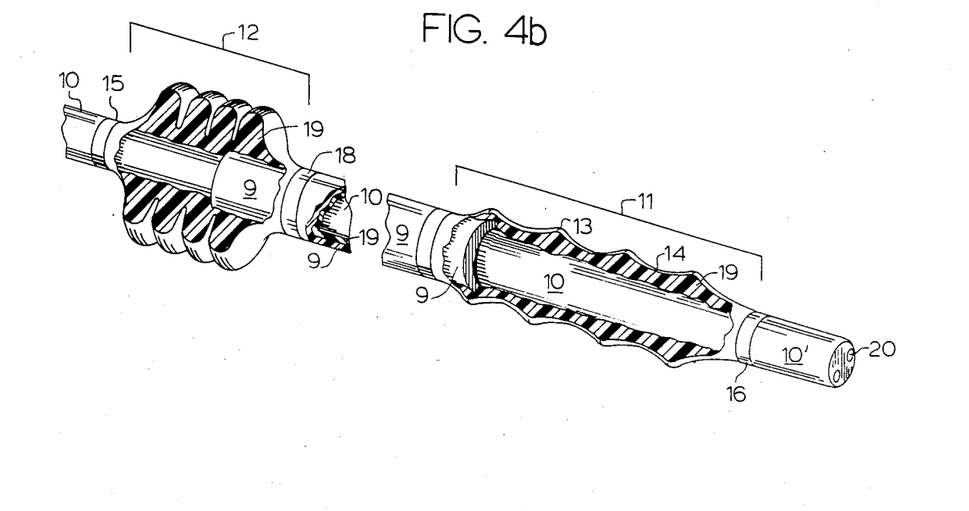

By use of any one of the embodiments of the disclosed invention, the painful experience that the patient must be put through and the training required of the practitioner as was the case with prior art endoscopes is not necessary because the colon loops do not need to be straightened out. The endoscope of the present invention (all three embodiments) using the recommended procedures will follow the curves of the colon as they appear with minimal pain and discomfort to the patient. This is best illustrated by the embodiment of FIGS. 3, 4(a) and 4(b) and the manner of use shown in FIGS. 9(a), 9(b) and 9(c). A comparison of FIGS. 1(a) through 1(e) to FIGS. 9(a) through 9(c) readily shows the difference in procedure of use between the prior art devices and the invention respectively. The flexible tube member of the endoscope of the present invention follows the loops and contures of the colon and does not require the sigmoid loop or any loops be "straightened out" before the tube portion of the three embodiments of the present invention can be inserted into the very deepest regions of the organs sought to be examined.

Referring to FIG. 2, there is shown by element 6 the first embodiment of the invention. Control portion 8, which is of prior art design and contains the customary view piece 30 with well known control knobs the description of which serves no part of the instant invention (see description of same in previously identified prior art patents), is optically connected to a first elongated flexible tube member 10, at junction 27. Elongated flexible tube member 10 contains prior art optical means (not shown) and is composed of a proximate end portion (adjacent element 27), and a distal portion 10' connected by a body portion (that portion of element 10 between the distal and proximate end portions). Distal end portion 10' is movable up, down, left and right and contains viewing and illuminating elements 20. Such elements (fiber optic in nature) are a means to transmit light to the interior of the organ being examined as well as a means to view the interior surface of the organ. All of this takes place in a prior art manner via fiber optic means (not shown) in the body and proximate portions of flexible tube 10, through viewer means 30 and a light source in control means 8. Movement of distal portion 10' is accomplished by rotating appropriate knobs that control cables (not shown) in the interior of tube 10 and 10' in a known prior art manner. Elongated flexible tube member 10 is nested inside and circumscribed by flexible tube means 9. Tube 9 has one free proximate end 31 spaced apart from control means 8 and a distal end portion (near element 17) fixedly attached to a distal accordion or bellows shaped means 11 at a point indicated by element 17. Distal bellows or accordion shaped means 11 is also affixed to tube 10 at a point adjacent to the distal portion 10', at a location indicated by element 16. Tube 9 is adapted to reciprocate in a coaxial fashion along its own and flexible tube member 10 longitudinal axis, the reciprocation taking place to the extent that the bellows portion 11 (shown in a compressed state) can be extended and compressed in the fashion as shown by element 11 of FIGS. 4(a) and 4(b). In between the innermost surfaces of second tube member 9 and element 11 and the outermost surface of tube member 10 may be some suitable lubricant, much in the matter as shown in FIG. 4(a). The internal optical and control cable construction of tube 10 in combination with control unit 8 is common for this and all hereinafter described embodiments.

A second embodiment is shown by element 7 of FIG. 3. This embodiment includes the same elements described in first embodiment 6, and in addition thereto contains a second but a proximate bellows or accordion means denoted by element 12. It will be noted that proximate bellows means 12 (like element 11) has plurality of ridges 13 and valleys 14 to form the accordion or bellows type structure and is, like distal bellows or accordion means 11, adapted to expand and contract upon movement of tube 9 while holding stationary tube member 10 and visa versa. Proximate bellows means 12 is affixed to first flexible tube member 10 at the point indicated by element 15 (near the proximate end portion of flexible tube 10) and is also affixed to second flexible tube member 9 at the point indicated by element 18, i.e., its proximate end portion. The space delimited by and between elements 9, 10, 11 and 12, as more fully described, may be filled with a suitable grease or lubricant.

The basic operation of embodiments shown by elements 6 and 7 is as follows: holding tube member 10 stationary, second tube member 9 is advanced thereover to the extent that distal bellows means 11 can be compressed and/or proximate bellows means 12 can be extended. Bellows or accordion means 11 and 12 are usually of the same construction and length and therefore they cooperate with one another in extending and contracting. Once tube member 9 has been advanced as far as distal bellows means 11 will permit and/or proximate bellows means 12 can be extended, then tube member 9 is held stationary while tube member 10 is advanced a distance that either the compression of proximate means 12 will permit or the extension of distal means 11 will allow. This "inchworm" expansion and contraction is repeated over and over and over again and by this repetition, the distal end 10' is advanced a short distance each expansion and contraction until finally reaches its destination point within the organ sought to be examined.

Reference is made to FIGS. 4(a) and 4(b) for a more detailed and graphic representation of this expansion and contraction characteristic of elements 11 and 12 of element 7. If distal bellows or accordion means 11 is compressed as per the manner previously described, the proximate bellows or accordions means 12 is extended and vis versa. The space delimited by the inner surface of bellows or accordion means 11 and 12 and outer surface of flexible tube member 10 and the inner surface of tube member 9 may be filled with a prior art lubricant such as petrolatum or mineral oil, shown by element 19. When tube member 9 is held stationary and tube member 10 (of which one terminal portion contains distal member 10') is pushed forward, extended proximate bellows means 12 of FIG. 4(a) will then compress to the compressed configuration of FIG. 4(b) and the compressed distal bellows or accordion means 11 of FIG. 4(a) will be extended, as shown in the FIG. 4(b).

Figures 5, 6A, 6B:
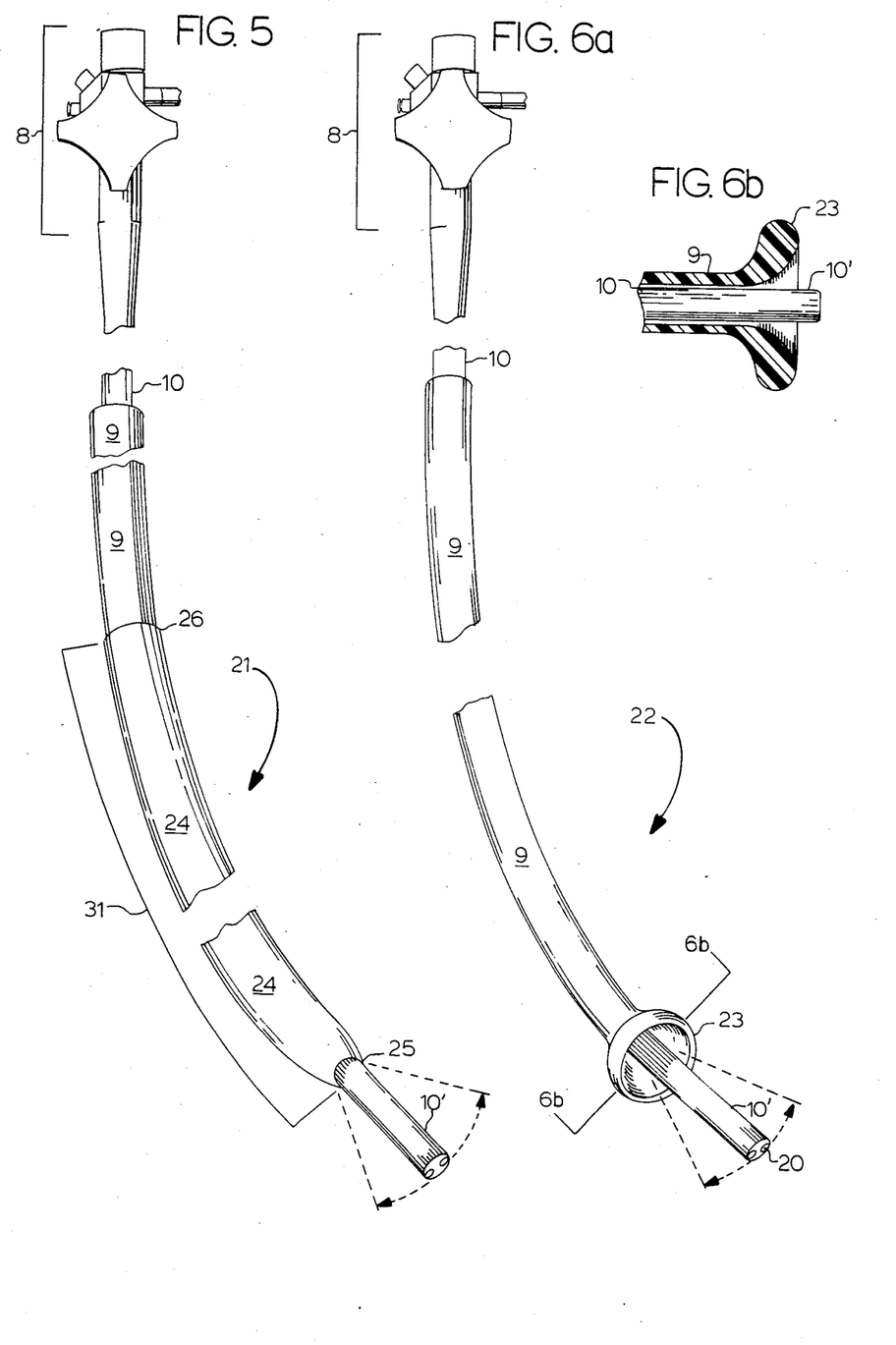
FIG. 5 is an oblique external view of the third embodiment of the invention.
FIG. 6(a) is an oblique external view of the fourth embodiment of the invention.
FIG. 6(b) is a partial cross section view of the distal end portion of the embodiment shown in FIG. 6(a) among lines 6b—6b.

Shown by element 21 of FIG. 5 is a third embodiment of the present invention, which also contains a control unit 8, joined to a flexible tube member 10 at its proximate end, and is composed of a body portion, reciprocating end portion 31 and distal portion 10'. Flexible tube member 9 circumscribes and has nested therein flexible tube member 10, which has a body portion connecting proximate end portion (portion nearest control unit 8) and distal end portion [portion nearest free edge 27, FIG. 7(b)]. Reciprocating end portion 31 is composed of tubular member 24, one end of which is fixedly attached to tube member 10 where tube member 10 joins distal portion 10'. The sidewall of tube member 24 [see FIGS. 7(a) and 7(b)] extends coaxially along the longitudinal axis of flexible tube member 10 to that point shown by element 26, the terminal free edge of flexible tube member 24. Terminal free edge 27 of flexible tube member 9 can be spaced apart from that point 25 where tube 24 is attached to tube 10. By comparing the location of free edge 27 of tube member 9 of FIG. 7(a) with the location of terminal free edge of 27 of tube 9 in FIG. 7(b), one can grasp the teaching that tube member 9 can be reciprocated from a first to a second position within the confines of third tube member 24. A stop means (not shown) may be placed on the outer surface of tube 9 and inner surface of tube 24 near free edge 26 to keep the free edge 27 of tube 9 within the confines of tube 24.

Figures 7A, 7B:
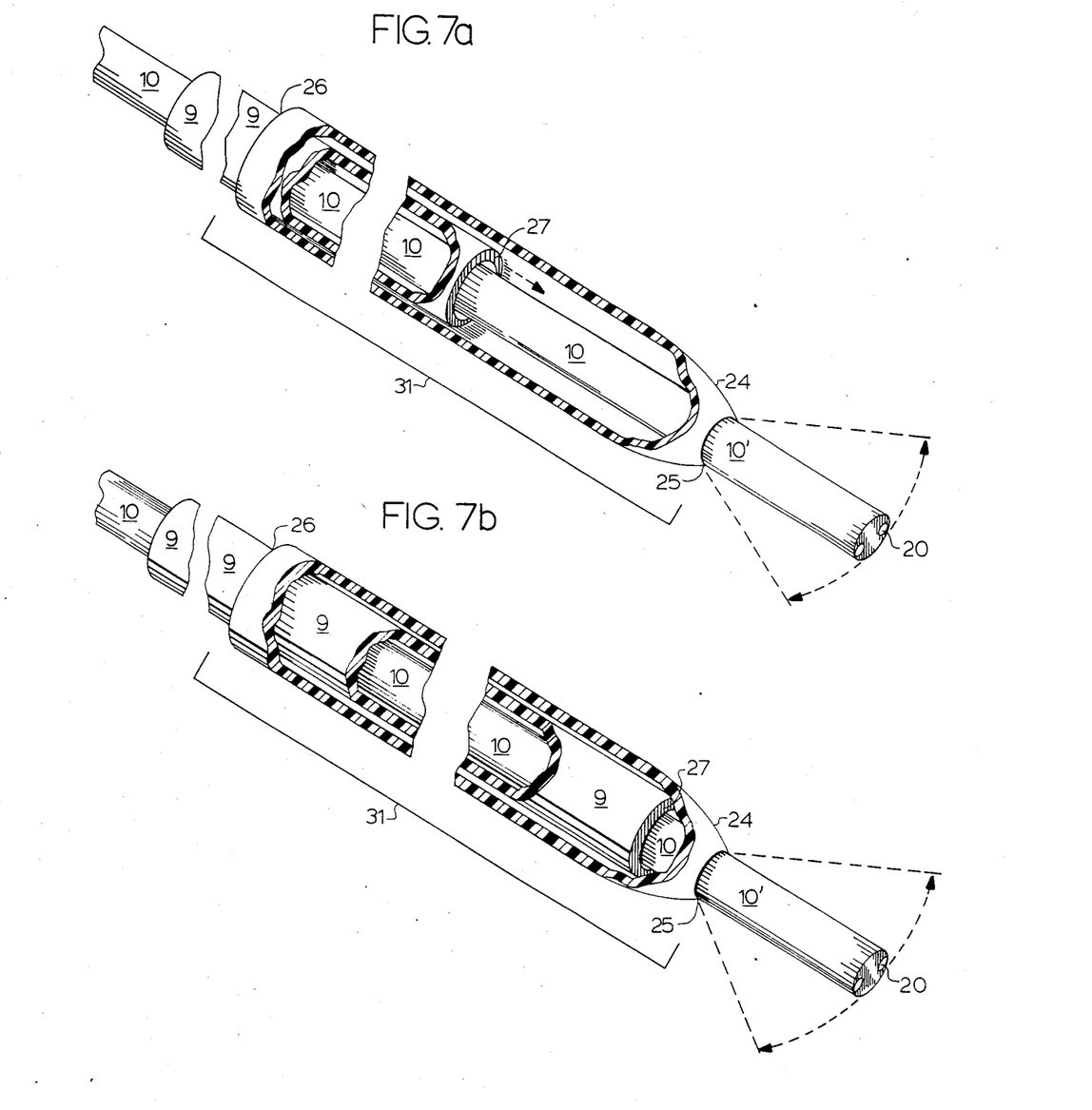
FIG. 7(a) is a partial cutaway oblique view of the distal end portion of the third embodiment of the invention shown in FIG. 5 showing tube 27 in a first position.
FIG. 7(b) is a partial cutaway oblique view of the distal end portion of the third embodiment of the invention shown in FIG. 7(b) with tube 27 shown in a second position.

Using the embodiment shown by element 21 of FIG. 5 and the teachings of its reciprocating manipulation as shown in FIGS. 7(a) and 7(b), one can readily realize that after insertion into an organ sought to be examined, by holding stationary tube 9, tube 10 and 10' can be advanced to that position as shown in FIG. 7(a). Then, by holding stationary tube 10, tube 9 can be advanced to that position as shown in FIG. 7(b). Repetition of such procedure, much like the "inchworm" manner as previously described for the first and second embodiments of the invention, causes the distal portion 10' to be advanced along loops and curves and twists and turns of the organ cavity of an animal or human to reach the deepest regions thereof, without having to straighten out any loops or curves as was the case with prior art devices, and without trapping organ matter (tissue) between the elements 9 and 10.

Figure 8A:
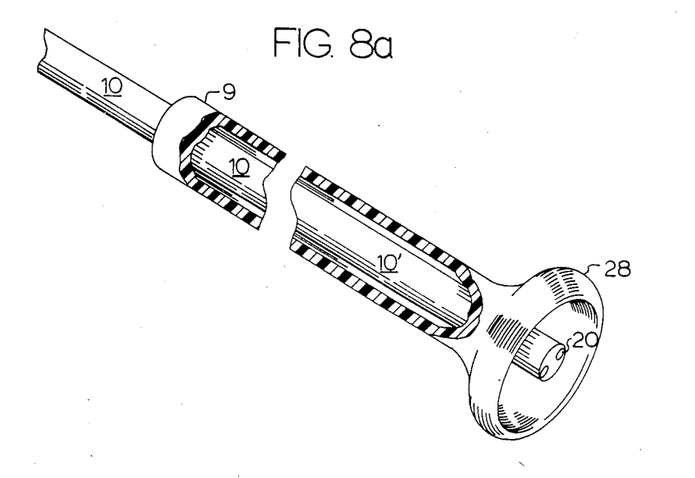
FIG. 8(a) is a partial cutaway oblique view of the distal end portion of the fourth embodiment of the invention first shown in FIG. 6 showing tube 10 and 10' in a first position.
Figure 8B:
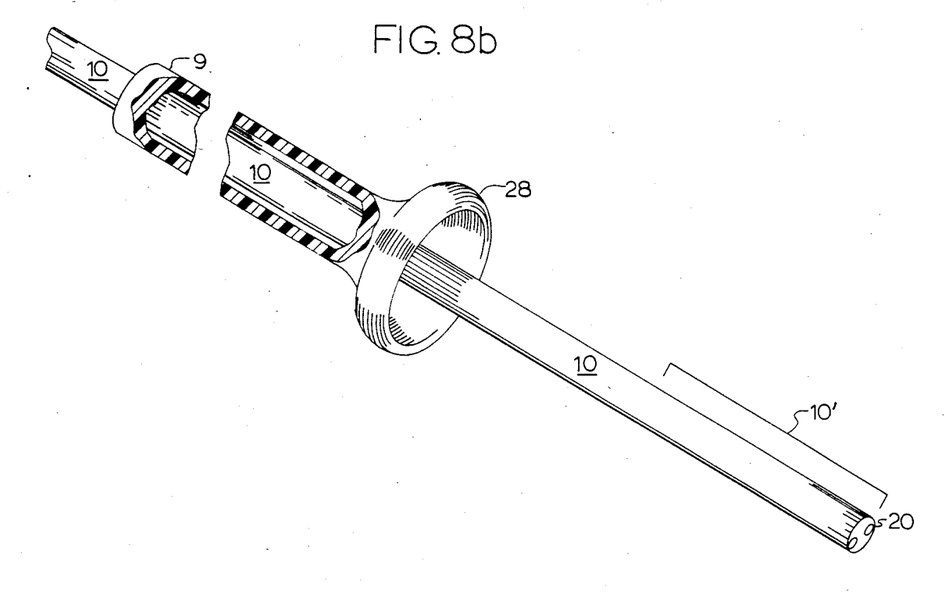
FIG. 8(b) is a partial cutaway oblique view of the distal end portion of the fourth embodiment of the invention shown in FIG. 8(a) showing tube 10 and 10' in a second position.

Another embodiment of this invention is shown by element 22 in FIGS. 6(a) and 6(b). Like previously described embodiments, it is composed of a control unit 8, flexible tube member 10 having a body portion connected to proximate and distal end portions (the proximate end portion is connected to control unit 8) and a second flexible tube member 9. Tube member 10 is coaxially nested inside of flexible tube member 9. Tube member 9 has an outward flaring distal end portion 23 and a proximate end portion having a free edge. In cross section, the distal end portion looks much like a "dog bone," a more detailed description being shown in FIGS. 6(b), 8(a) and 8(b). In use, flexible tube member 10 is inserted into the organ sought to be examined and advanced a short distance while second flexible tube member 9 is held stationary. After such advancement, the process is reversed, i.e., second flexible tube member 9 is advanced a short distance while holding stationary flexible tube 10. Thereafter, this process is repeated over and over again, advancing first one and then the other into the organ sought to be examined to the situs within the organ sought to be examined. The "dog bone" flaring distal portion of flexible tube member 9 tends to push the sidewalls of the organ away from and allows free movement of tube member 10, which then can be moved without hindrance at least to a position co-extensive with the terminal free edge of distal portion 28 of second flexible tube member 9. The process is then repeated until the desired location within the organ to be examined is reached.

Figure 10A:
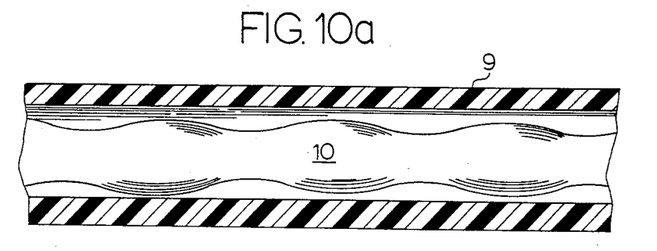
FIGS. 10(a), 10(b) and 10(c) are partial cross sections of various embodiments of flexible tubes 9 and 10.
Figure 10B:
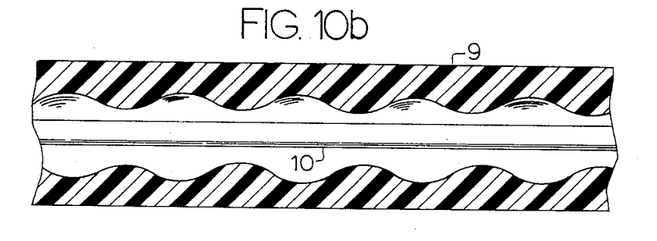
Figure 10C:
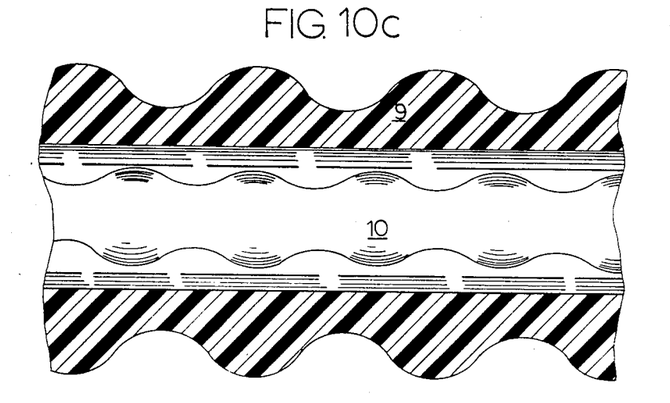

Friction is always an important consideration whenever one surface is moved across another. When a foreign body, such as tube 9 is inserted into an organ (for example, a colon) for examination, friction between flexible tube 9 and the organ and flexible tube 9 and flexible tube 10 becomes a factor worthy of consideration. With respect to FIG. 10(a), an embodiment is shown whereby tube 10 can be so constructed to have an undulating outer surface and the inner and outer surface of tube 9 being straight. Such a construction reduces friction between the outermost surface of tube 10 and the innermost surface of tube 9. With respect to FIG. 10(b), another embodiment is shown whereby the innermost surface of flexible tube 9 is undulating and the outermost surface of flexible tube 10 is straight. Such a construction reduces friction between the two tubes, whenever they are moved relative to one another. In FIG. 10(c) still another embodiment is shown whereby the outermost surfaces of both flexible tubes 9 and 10 are undulating. Such a construction not only reduces friction between the two tubes 9 and 10, but also between tube 9 and the sidewall of the organ undergoing examination. Various prior art lubricants may be used in that space delimited by the innermost surface of tube 9 not otherwise occupied by flexible tube 10 as well as on the outermost surface of flexible tube 9. Undulating surfaces of flexible tubes 9 and 10 [as shown in FIGS. 10(a), 10(b) and 10(c)] may be either longitudinal (not shown) or helical (as shown) and for best results face a smooth surface such as another tube or an organ sidewall.

Figure 9A:
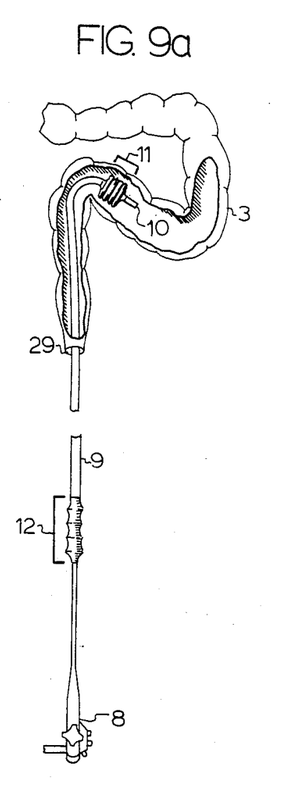
FIGS. 9(a), 9(b) and 9(c) are graphic representations of the second mentioned embodiment of the invention showing how it is inserted and advanced in a human colon and through the first encountered loop without having to straighten out the loop and on into the deeper regions of the colon, the colon retaining its original configuration.
Figure 9B:
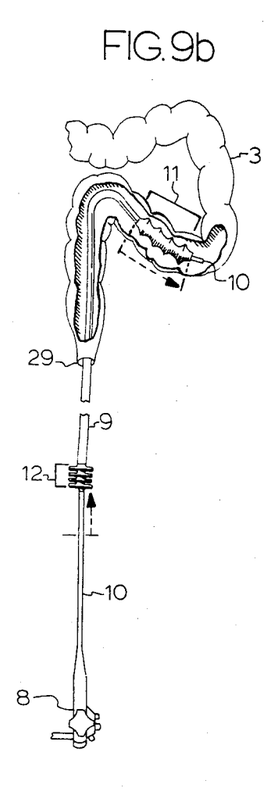
Figure 9C:
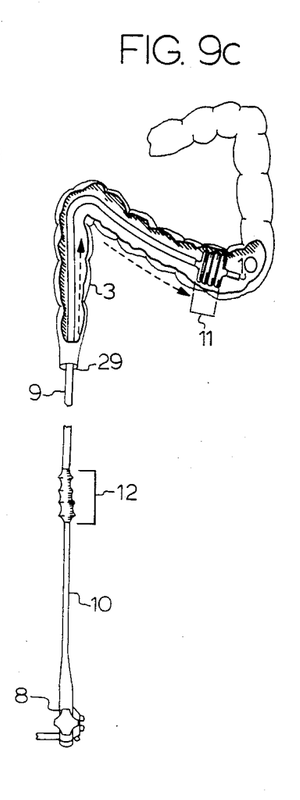

Associated with the description of the structure of each of the three embodiments of this invention, a brief description of the manner which that embodiment was used in actual practice has been described and it will be noted that there is a procedure common to all embodiments, namely a movement of one tube a short distance, then the other coaxially sliding in or over the first tube and then a repetition of this process until the desired location is reached within the organ. FIGS. 9(a), 9(b) and 9(c) graphically represent the procedures thus described employing embodiment of element 7. Element 29 represents the opening in an animal's body, in this instance, the anus of a human colon and embodiment number 2 (element 7) is shown therein as an example for fully understanding of the method of operation (use) of three embodiments of the instant invention, all of which are operated in essentially the same manner. It will be remembered that compression of distal accordion or bellows means 11 requires an expansion of proximate accordion or bellows means 12, as shown in FIG. 9(a). The distal portion 10' is advanced through the colon a short distance, that short distance being delimited by the amount of linear distance that distal bellows or accordion means 11 expands and/or proximate accordion or bellows means 12 is contracted into a compressed state. See FIG. 9(b). Operation of this particular embodiment starts from that state of the instrument shown in FIG. 9(a) to that state shown in FIG. 9(b) and is achieved by first holding stationary tube 10 and pushing tube member 9 as far as it will go thereby compressing distal bellows or accordion means 11 and simultaneously extending proximate bellows or accordion means 12. Subsequently, while holding tube member 9 stationary, tube member 10 is then advanced as far as the expansion of distal bellows or accordion means 11 and compression of proximate means 12 will permit thereby achieving the state as shown in FIG. 9(b). The procedure is then reversed and the configuration of the bellows or accordion means 11 and 12 and the position of distal means 10' is shown in FIG. 9(c), which is the same as that shown in FIG. 9(a) except for the advancement of distal member 10 along colon 3. This process is repeated over and over again to the desired location and it has been found by Applicant that distal member 10' will follow the curvilinear configurations of colon 3 to its deepest regions without requiring first straightening out any such loops or bends thereby permitting examination of those deep within the colon regions by control means 8 (view piece 31) and distal member 10' via the optical means within the body and proximate portion of tube 10.

What is claimed is:
1. An endoscope comprising:
   (a) a control unit;
   (b) a first flexible tube member having a proximate end portion in optical communication with the control unit, a body portion and a distal end portion having a free end containing means therein to transmit light to and from said control unit so that images outside of the distal portion may be illuminated and viewed through the control unit and the proximate end portion;
   (c) a second flexible tube member having a proximate and distal end portions and a body portion partially circumscribing the body portion of said first tube member; and,
   (d) a first expansion and contraction means attached to the distal end portion of the second flexible tube member and to the first flexible tube member at a point other than its distal portion so that it will expand and contract along its own and the longitudinal axis of the first and second flexible tube members.
2. The endoscope of claim 1 containing a second expansion and contraction means attached to the proximate end portion of the second flexible tube member and to the proximate end portion of the first flexible tube member.
3. The endoscope of claims 1 or 2 wherein the inner surface of the second flexible tube member is undulating.
4. The endoscope of claims 1 or 2 wherein the outer surface of the first flexible tube member is undulating.
5. The endoscope of claims 1 or 2 wherein both inner and outer surfaces of the second flexible tube member is undulating.
6. The endoscope of claim 2 wherein the longitudinal distance the first and second expansion and contraction means may expand and contract are essentially equal.
7. The endoscope of claims 1, 2 or 6 wherein the space delimited by the second flexible tube and the first and second expansion and contraction means not otherwise occupied by the first flexible tube member is essentially occupied by a lubricant.
8. An endoscope comprising:
   (a) a control unit;
   (b) a first flexible tube member having a proximate end portion in optical communication with the control unit, a body portion and a distal end portion having a free end containing means therein to transmit light to and from said control unit so that images outside of the distal portion may be illuminated and viewed through the control unit and the proximate end portion;
   (c) a second flexible tube member having a body portion, distal and proximate end portions, partially circumscribing said first tube member; and,
   (d) a third flexible tube member (i) having one terminal end portion affixed to the first flexible tube member at a point other than its distal portion and a body portion having a free edge spaced apart from and opposite from such point; (ii) the body portion of the third flexible tube member being spaced apart from, coaxial with and circumscribing the distal portion of the second flexible tube member and a portion of the body portion of said first flexible tube member adjacent to its distal portion, so that the distal end portion of the second flexible tube member is slideably received in the third flexible tube member and may be moved reciprocally therein from the point where the third flexible tube member is affixed to the first flexible tube member and its free edge.
9. The endoscope of claim 8 wherein the innermost surface of the second flexible tube member is undulated.
10. The endoscope of claim 8 wherein the inner and outermost surfaces of the second flexible tube member are undulating.
11. An endoscope comprising:
   (a) a control unit;
   (b) a first flexible tube member having a proximate end portion in optical communication with the control unit, a body portion and a distal end portion having a free end containing means therein to transmit light to and from said control unit so that images outside of the distal portion may be illuminated and viewed through the control unit and the proximate end portion; and,
   (c) a second flexible tube member partially circumscribing the body portion of the first flexible tube member having free proximate and distal end portions, the distal end portion comprising an outward flaring sidewall the thickness thereof being greater than the thickness of the body portion of the second flexible tube member sidewall.
12. The endoscope of claim 11 wherein the inner surface of the second flexible tube member is undulating.
13. The endoscope of claim 11 wherein the inner and outermost surface of the second flexible tube member is undulating.

* * * * *